(12) United States Patent
Chung et al.

(10) Patent No.: US 8,445,578 B2
(45) Date of Patent: *May 21, 2013

(54) COMPOSITIONS FOR FORMING REFLECTING LAYER HAVING ORGANIC SILVER COMPLEXES, AND METHOD FOR PREPARING REFLECTING LAYER USING SAME

(75) Inventors: Kwang-Choon Chung, Gyeonggi-do (KR); Hyun-Nam Cho, Gyeonggi-do (KR); Seong-Yong Uhm, Gyeonggi-do (KR); Young-Kwan Seo, Gyeonggi-do (KR)

(73) Assignee: Inktec Co., Ltd., Kyeongki-do (KR)

( * ) Notice: Subject to any disclaimer, the term of this patent is extended or adjusted under 35 U.S.C. 154(b) by 959 days.

This patent is subject to a terminal disclaimer.

(21) Appl. No.: 12/226,779

(22) PCT Filed: Apr. 27, 2007

(86) PCT No.: PCT/KR2007/002104
§ 371 (c)(1),
(2), (4) Date: May 15, 2009

(87) PCT Pub. No.: WO2007/126276
PCT Pub. Date: Nov. 8, 2007

(65) Prior Publication Data
US 2009/0220696 A1 Sep. 3, 2009

(30) Foreign Application Priority Data
Apr. 29, 2006 (KR) .................... 10-2006-0039107

(51) Int. Cl.
*C04B 28/14* (2006.01)

(52) U.S. Cl.
USPC ........ 524/423; 556/110; 556/13; 106/287.18; 106/285; 427/419.8

(58) Field of Classification Search
USPC ........................................... 524/423
See application file for complete search history.

(56) References Cited

U.S. PATENT DOCUMENTS
8,226,755 B2 * 7/2012 Chung et al. ............ 106/1.19
2006/0081457 A1 * 4/2006 Butz et al. ............... 204/192.1

FOREIGN PATENT DOCUMENTS
| JP | 60-243277 A | 12/1985 |
| JP | 61-163975 | 7/1986 |
| JP | 3-179063 | 8/1991 |
| JP | 2002-129259 | 5/2002 |
| JP | 2005-157296 | 6/2005 |
| WO | 02/04700 | 1/2002 |
| WO | 2006/020584 | 2/2006 |

* cited by examiner

Primary Examiner — Doris Lee
(74) Attorney, Agent, or Firm — Clark & Brody (57) ABSTRACT

The present invention relates to compositions for forming reflecting layer having organic silver complexes, and method for preparing reflecting layer using the same. More specifically, it relates to compositions for forming reflecting layer including silver complexes that have distinct structures and the method for preparing reflecting layer, where primary coating is applied to promote the adhesive force to materials such as plastic, ceramic, metal, etc. and then a high-reflecting layer is formed by using the silver coating fluid, followed by transparent coating for protection.

25 Claims, 5 Drawing Sheets

COMPOSITIONS FOR FORMING REFLECTING LAYER HAVING ORGANIC SILVER COMPLEXES, AND METHOD FOR PREPARING REFLECTING LAYER USING SAME

TECHNICAL FIELD

The present invention relates to compositions for forming reflecting layer having organic silver complexes, and method for preparing reflecting layer using the same. More specifically, it relates to compositions for forming reflecting layer including silver complexes that have distinct structures and the method for preparing reflecting layer using the same, where primary coating is applied to promote the adhesive force to materials such as plastic, ceramic, metal, etc. and then a high-reflecting layer is formed by using the silver coating fluid, followed by transparent coating for protection.

BACKGROUND ART

While industries are developing rapidly, the needs for reflecting layers also grow in all aspects including mobile phones, MP3, displays, lamp housing, lamp reflectors, etc. Usually, the form of reflecting layers varies from flat ones such as sheets and plates to complicated forms by the press process. As materials, silver, aluminum, copper, rhodium, platinum are used, which have high reflectance. In spite of excellent reflecting properties, such metal materials usually have low chemical stability and are difficult to be processed to surface state with high illuminance and great reflectance. They are also heavy and disadvantageous in terms of price, so there are some problems to process metal materials directly to reflecting layers.

Japanese Laid-Open Patent Publication No. PYUNG2005-157296 discloses the preparation method of white reflecting layers by powder coating using titanium dioxide ($TiO_2$). There are similar methods that form white reflecting layers by coating paints including pigments of metallic oxide such as silane oxide, titanium dioxide, magnesium oxide, and barium oxide directly on metal plates, but they have some disadvantages of low reflectance and poor weather resistance.

Also, when materials such as silver (Ag) or chromium (Cr) are used, reflecting layers having advanced-quality surface gloss and high reflectance can be obtained. However, there are often defective proportions during production and plating costs too much, which could lead to air pollution and waste water due to discharge of noxious substance.

On the other hand, Japanese Laid-Open Patent Publication No. PYUNG2002-129259 discloses the preparation method of high reflecting layers by vacuum evaporation using silver as its main component. After vacuum evaporation using high reflecting metals including silver (Ag), aluminum (Al), nickel (Ni), rhodium (Rh) on the surface of flexible materials such as PET, reflecting layers can be made through laminating on the support. However, there are a few disadvantages that vacuum evaporation needs a high vacuum chamber and it may restrict the form and size of the material and make coating thickness not uniform, and the equipment costs a lot, too.

DISCLOSURE

Technical Problem

To solve such problems, the inventors have put enormous efforts and finally came up with the present invention.

The present invention provides silver coating compositions and its preparation method of reflecting layers using the same, which can produce high-reflecting layers after forming primary coating layers that promote illuminance and adhesive force of reflecting materials such as plastic, ceramic, metal, etc., and then forming high-reflecting layers by coating silver coating fluid including silver complexes with distinct structures, followed by transparent-coating to protect the silver specular surface.

Also, the present invention provides silver coating compositions and preparation methods of reflecting layers using them, which can be mass manufactured with no risk of air pollution or water contamination and have low defective proportions and inexpensive production costs due to simple manufacturing process.

Technical Solution

The present invention relates to compositions for forming reflecting layer having organic silver complexes and method for preparing reflecting layer using the same. Hereinafter, the present invention is described in more detail.

The compositions for forming reflecting layer according to the present invention comprise the silver complexes that are obtained by the reaction between the silver compound (Formula 1) and ammonium carbamate or ammonium carbonate based compounds (Formula 2 to 4).

[In the formula above,

X is a substituted group selected from the group consisting of oxygen, sulfur, halogen, cyano, cyanate, carbonate, nitrate, nitrite, sulfate, phosphate, thiocyanate, chlorate, perchlorate, tetrafluoro borate, acetylacetonate, carboxylate and their derivatives, n is an integer of 1~4, $R_1$ to $R_6$ are substituted groups independently selected from the group consisting of hydrogen, C1-C30 of aliphatic or cycloaliphatic alkyl group or aryl or aralkyl group, alkyl and aryl group substituted with functional group, heterocyclic compound, polymer compound and their derivatives.]

In the formula 1 above, n is an integer of 1~4, X is a substituted group selected from the group consisting of oxygen, sulfur, halogen, cyano, cyanate, carbonate, nitrate, nitrite, sulfate, phosphate, thiocyanate, chlorate, perchlorate, tetrafluoro borate, acetylacetonate, carboxylate and their derivatives, for example, silver oxide, silver thiocyanate, silver sulfide, silver chloride, silver cyanide, silver cyanate, silver carbonate, silver nitrate, silver nitrite, silver sulfate, silver phosphate, silver perchlorate, silver tetrafluoro borate, silver acetylacetonate, silver acetate, silver lactate, silver oxalate and their derivatives, but it is not specially defined to the compounds above.

And, $R_1$, $R_2$, $R_3$, $R_4$, $R_5$ and $R_6$ can be independently selected from the group consisting of hydrogen, methyl, ethyl, propyl, isopropyl, butyl, isobutyl, amyl, hexyl, ethylhexyl, heptyl, octyl, isooctyl, nonyl, decyl, dodecyl, hexadecyl, octadecyl, docodecyl, cyclopropyl, cyclopentyl, cyclohexyl, allyl, hydroxy, methoxy, hydroxyethyl, methoxyethyl, methoxypropyl, cyanoethyl, ethoxy, buthoxy, hexyloxy, methoxyethoxyethyl, methoxyethoxyethoxyethyl, hexamethyleneimine, morpholine, piperidine, piperazine, ethylenediamine, propylenediamine, hexamethylenediamine, triethylenediamine, pyrrol, imidazol, pyridine, carboxymethyl, trimethoxysilylpropyl, triethoxysilylpropyl, phenyl, methoxyphenyl, cyanophenyl, phenoxy, tolyl, benzyl and their derivatives, and polymer compounds such as polyallylamine or polyethyleneimine and their derivatives, but it is not specially defined to the compounds above. As the concrete compounds, for example, they are one or more than two mixture selected from the group consisting of ammonium carbamate, ammonium carbonate, ammonium bicarbonate, ethylammonium ethylcarbamate, isopropylammonium isopropylcarbamate, n-butylammonium n-butylcarbamate, isobutylammonium isobutylcarbamate, t-butylammonium t-butylcarbamate, 2-ethylhexylammonium 2-ethylhexylcarbamate, octadecylammonium octadecylcarbamate, 2-methoxyethylammonium 2-methoxyethylcarbamate, 2-cyanoethylammonium 2-cyanoethylcarbamate, dibutylammonium dibutylcarbamate, dioctadecylammonium dioctadecylcarbamate, methyldecylammonium methyldecylcarbamate, hexamethyleneimineammonium hexamethyleneiminecarbamate, morpholinium morpholinecarbamate, pyridinium ethylhexylcarbamate, triethylenediaminium isopropylbicarbamate, benzylammonium benzylcarbamate, triethoxysilylpropylammonium triethoxysilylpropylcarbamate, ethylammonium ethylcarbonate, isopropylammonium isopropylcarbonate, isopropylammonium bicarbonate, n-butylammonium n-butylcarbonate, isobutylammonium isobutylcarbonate, t-butylammonium t-butylcarbonate, butylammonium bicarbonate, 2-ethylhexylammonium 2-ethylhexylcarbonate, 2-ethylhexylammonium bicarbonate, 2-methoxyethylammonium 2-methoxyethylcarbonate, 2-methoxyethylammonium bicarbonate, 2-cyanoethylammonium 2-cyanoethylcarbonate, 2-cyanoethylammonium bicarbonate, octadecylammonium octadecylcarbonate, dibutylammonium dibutylcarbonate, dioctadecylammonium dioctadecylcarbonate, dioctadecylammonium bicarbonate, methyldecylammonium methyldecylcarbonate, hexamethyleneimineammonium hexamethyleneiminecarbonate, morpholineammonium morpholinecarbonate, benzylammonium benzylcarbonate, triethoxysilylpropylammonium triethoxysilylpropylcarbonate, pyridinium bicarbonate, triethylenediaminium isopropylcarbonate, triethylenediaminium bicarbonate and their derivatives.

On the other hand, it doesn't necessarily have to restrict the kind of ammonium carbamate or ammonium carbonate based compounds and their manufacturing methods. For example, U.S. Pat. No. 4,542,214 (1985. 9. 17) discloses that ammonium carbamate based compounds can be prepared from primary amine, secondary amine, tertiary amine or at least one of these compounds and carbon dioxide. Ammonium carbonate based compounds can be obtained if 0.5 mole of water is added per one mole of amine, and ammonium bicarbonate based compounds can be obtained if more than one mole of water is added. In case they are made with or without any specific solvent in the condition of pressure or ambient pressure, the followings are to be used: water, alcohols such as methanol, ethanol, isopropanol and butanol, glycols such as ethyleneglycol and glycerine, acetates such as ethyl acetate, butyl acetate and carbitol acetate, ethers such as diethyl ether, tetrahydrofuran and dioxane, ketones such as methyl ethyl ketone and acetone, hydrocarbons such as hexane and heptane, aromatic compounds such as benzene and toluene, halogen substituted solvents such as chloroform, methylene chloride and carbontetrachloride, or mixed solvents of the above. As for carbon dioxide, it can be used as bubbled ones in the vapor phase or as solid dry ices. It can react in the supercritical condition, too. To prepare ammonium carbamate or ammonium carbonate derivatives that are used in the present invention, it is fine to use any methods including the above ones, if the final material structure is identical. In other words, it doesn't necessarily have to put restrictions on solvents, reaction temperature, concentration, catalyst, etc. for preparation and its yield.

Organic silver complexes can be manufactured by reaction between ammonium carbamate or ammonium carbonate based compounds and silver compounds. For instance, the preparation takes at least one silver compound as shown in Formula 1 and at least one ammonium carbamate or ammonium carbonate derivatives as shown in Formula 2 to 4 and the complex of these, which react by themselves without solvents in the nitrogen condition of pressure or ambient pressure. In case solvents are used, the followings can be used: water, alcohols such as methanol, ethanol, isopropanol and butanol, glycols such as ethyleneglycol and glycerine, acetates such as ethyl acetate, butyl acetate and carbitol acetate, ethers such as diethyl ether, tetrahydrofuran and dioxane, ketones such as methyl ethyl ketone and acetone, hydrocarbons such as hexane and heptane, aromatic compounds such as benzene and toluene, and halogen substituted solvents such as chloroform, methylene chloride, carbontetrachloride, or mixed solvents of the above.

To prepare silver complexes that are used in the present invention, besides the above methods, it can be manufactured by preparing a mixed solution of silver compound (Formula 1) and at least one amine compound and then making it react with carbon dioxide. Like above, it can react either with or without solvents in the nitrogen condition of pressure or ambient pressure. However, it is fine to use any methods if the final material structure is identical. In other words, it doesn't necessarily have to put restrictions on solvents, reaction temperature, concentration, catalyst, etc. for preparation and its yield.

The manufacturing method of the silver complexes according to the present invention is disclosed in Korean Patent Application No. 10-2006-0011083 by the inventors of the present invention. It has the structure of Formula 5 below.

$$Ag[A]_m \hspace{2cm} \text{[Formula 5]}$$

[A is the compound of Formula 2 to 4, and m ranges in 0.5~1.5.]

The silver coating composition used to form the reflecting layer (2) with high reflectance and high gloss includes the silver complex above. The coating composition of the present invention may include additives such as solvents, stabilizers, leveling agents, and film assistants, if necessary.

As for stabilizers, for instance there are amine compounds such as primary amine, secondary amine, and tertiary amine; ammonium carbamate, ammonium carbonate, and ammonium bicarbonate based compounds; phosphorus compounds such as phosphine, phosphite, and phosphate; sulfur compounds including thiol and sulfide. They consist of these compounds or mixture of more than at least one of them. As the concrete amine compounds, for example, they are selected from the group consisting of methyl amine, ethyl amine, n-propyl amine, isopropyl amine, n-butyl amine, isobutyl amine, isoamyl amine, n-hexyl amine, 2-ethylhexyl amine, n-heptyl amine, n-octyl amine, isooctyl amine, nonyl amine, decyl amine, dodecyl amine, hexadecyl amine, octadecyl amine, docodecyl amine, cyclopropyl amine, cyclopentyl amine, cyclohexyl amine, allyl amine, hydroxy amine, ammonium hydroxide, methoxy amine, 2-ethanolamine, methoxyethyl amine, 2-hydroxypropyl amine, 2-hydroxy-2-methylpropyl amine, methoxypropyl amine, cyanoethyl amine, ethoxy amine, n-buthoxy amine, 2-hexyloxy amine, methoxyethoxyethyl amine, methoxyethoxyethoxyethyl amine, diethyl amine, dipropyl amine, diethanolamine, hexamethyleneimine, morpholine, piperidine, piperazine, ethylenediamine, propylenediamine, hexamethylenediamine, triethylenediamine, 2,2-(ethylenedioxy)bisethyl amine, triethyl amine, triethanolamine, pyrrol, imidazol, pyridine, aminoacetaldehyde dimethyl acetal, 3-aminopropyltrimethoxy silane, 3-aminopropyltriethoxy silane, aniline, anisidine, aminobenzonitrile, benzyl amine and their derivatives, and polymer compounds such as polyallylamine or polyethyleneimine and their derivatives. As the concrete compounds, for example, ammonium carbamate, ammonium carbonate, and ammonium bicarbonate based compounds are selected from the group consisting of ammonium carbamate, ammonium carbonate, ammonium bicarbonate, ethylammonium ethylcarbamate, isopropylammonium isopropylcarbamate, n-butylammonium n-butylcarbamate, isobutylammonium isobutylcarbamate, t-butylammonium t-butylcarbamate, 2-ethylhexylammonium 2-ethylhexylcarbamate, octadecylammonium octadecylcarbamate, 2-methoxyethylammonium 2-methoxyethylcarbamate, 2-cyanoethylammonium 2-cyanoethylcarbamate, dibutylammonium dibutylcarbamate, dioctadecylammonium dioctadecylcarbamate, methyldecylammonium methyldecylcarbamate, hexamethyleneimineammonium hexamethyleneiminecarbamate, morpholinium morpholinecarbamate, pyridinium ethylhexylcarbamate, triethylenediaminium isopropylbicarbamate, benzylammonium benzylcarbamate, triethoxysilylpropylammonium triethoxysilylpropylcarbamate, ethylammonium ethylcarbonate, isopropylammonium isopropylcarbonate, isopropylammonium bicarbonate, n-butylammonium n-butylcarbonate, isobutylammonium isobutylcarbonate, t-butylammonium t-butylcarbonate, t-butylammonium bicarbonate, 2-ethylhexylammonium 2-ethylhexylcarbonate, 2-ethylhexylammonium bicarbonate, 2-methoxyethylammonium 2-methoxyethylcarbonate, 2-methoxyethylammonium bicarbonate, 2-cyanoethylammonium 2-cyanoethylcarbonate, 2-cyanoethylammonium bicarbonate, octadecylammonium octadecylcarbonate, dibutylammonium dibutylcarbonate, dioctadecylammonium dioctadecylcarbonate, dioctadecylammonium bicarbonate, methyldecylammonium methyldecylcarbonate, hexamethyleneimineammonium hexamethyleneiminecarbonate, morpholium morpholinecarbonate, benzylammonium benzylcarbonate, triethoxysilylpropylammonium triethoxysilylpropylcarbonate, pyridinium bicarbonate, triethylenediaminium isopropylcarbonate, triethylenediaminium bicarbonate and their derivatives. Also, phosphorus compounds are represented as Formula $R_3P$, $(RO)_3P$, or $(RO)_3 PO$, where 'R' indicates alkyl or aryl group of carbon number 1~20, and the examples are tributyl phosphine, triphenyl phosphine, triethyl phosphite, triphenyl phosphite, dibenzyl phosphate, triethyl phosphate, etc. For sulfur compounds, there are butan thiol, n-hexanethiol, diethyl sulfide, tetrahydrothiophene, allyl disulfide, 2-mercaptobenzoxazole, tetrahydrothiophene, octylthioglycolate, etc. The amount of stabilizer usage is not limited once it is suited for the ink property of the present invention. Yet, it is good to have a mole ratio of 0.1%-90% to silver compounds. Also, for film assistants, organic acid and organic acid derivatives can be used and they are composed of mixture of more than at least one component. The examples of organic acid are acetic acid, butyric acid, valeric acid, pivalic acid, hexanoic acid, octanoic acid, 2-ethyl-hexanoic acid, neodecanoic acid, lauric acid, stearic acid, naphthalic acid, etc. For organic acid derivatives, there are organic acid ammonium salt such as ammonium acetate, ammonium citrate, ammonium laurate, ammonium lactate, ammonium maleate, ammonium oxalate, and ammonium molybdate; organic acid metal salts such as manganese oxalate, gold acetate, palladium oxalate, silver 2-ethyl hexanoate, silver octanoate, silver neodecanoate, cobalt stearate, nickel naphthalate, and cobalt naphthalate, which include such metals as Au, Cu, Zn, Ni, Co, Pd, Pt, Ti, V, Mn, Fe, Cr, Zr, Nb, Mo, W, Ru, Cd, Ta, Re, Os, Ir, Al, Ga, Ge, In, Sn, Sb, Pb, Bi, Sm, Eu, Ac, Th, etc. The usage amount of film assistants is not limited, but it is good to have a mole ratio of 0.1%~25% to silver complexes.

And, solvents may be sometimes needed to control the viscosity of silver coating composition or to help make thin film. The usable solvents can be selected from the group consisting of water, alcohols such as methanol, ethanol, isopropanol, 1-methoxypropanol, butanol, ethylhexyl alcohol, and terpineol, glycols such as ethyleneglycol and glycerine, acetates such as ethyl acetate, butyl acetate, methoxypropyl acetate, carbitol acetate, and ethylcarbitol acetate, ethers such as methyl cellosolve, butyl cellosolve, diethyl ether, tetrahydrofuran and dioxane, ketones such as methyl ethyl ketone, acetone, dimethylformamide, and 1-methyl-2-pyrrolidone, hydrocarbons such as hexane, heptane, dodecane, paraffin oil, and mineral spirits, aromatic compounds such as benzene, toluene, and xylene, halogen substituted solvents such as chloroform, methylene chloride and carbontetrachloride, acetonitrile, dimethylsulfoxide or mixed solvents of the above.

Now, the preparation method of reflecting layers is described in more detail using the composition for reflecting layers according to the present invention.

The preparation method of reflecting layers according to the present invention comprises the steps of: (i) forming at least one kind of primary coating layers, which improves illuminance of reflecting materials and the adhesion force of silver specular coating layers, and (ii) forming a reflecting layer coating a high-reflecting specular surface on the primary coating layer using the composition for reflecting layers according to the present invention, and more comprises the step of: (iii) forming at least one kind of transparent finish coating, which protects the reflecting layer and improves heat resistance, salt water resistance, and weather resistance.

Also, the present invention more comprises the steps where a pre-coat layer is formed to improve adhesion force and gloss and where a postcoat layer is formed by adding another transparent coating on the reflecting layer in order to improve adhesion force between the reflecting layer and transparent finish coating layer or to control transparency and color change.

Also, the present invention more comprises the step where the reflecting layer is adhered to supporters such as metal or ceramic layers using adhesives and then laminated.

Hereinafter, the present invention is described in more detail by the steps based on the figures.

Figure 1:
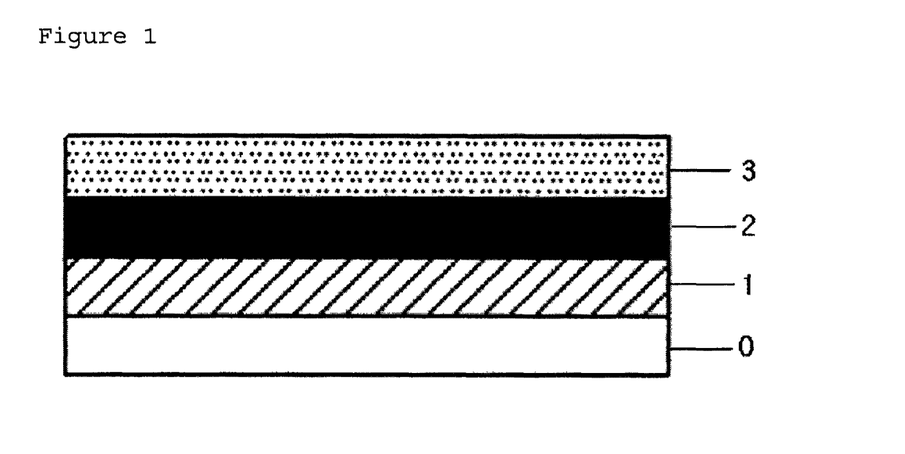
FIG. 1 is a cross section of a reflecting layer, which is composed of a primary coating layer (1), a reflecting layer (2), and transparent finish coating layer (3).

FIG. 1 is a cross section of a reflecting layer, which is composed of a primary coating layer (1), a reflecting layer (2), and transparent finish coating layer (3).

Step (i):

First, the primary coating layer (1) is formed, which promotes adhesion among materials and has high illuminance, after a primary paint was coated on the surface of materials such as plastic, ceramic, metal, etc.

The materials that can be used in the present invention are plastics such as acrylbutadienestyrene copolymer (ABS), polycarbonate (PC), polystyrene (PS), polymethylmethacrylate (PMMA), nylon, polybutyleneterephthalate (PBT), polyethyleneterephthalate (PET), polyethylenenaphthalate (PEN), polyetheretherketone (PEEK), polyimide (PI), etc.; metals including stainless, tin, aluminum, aluminum alloys, copper-zinc alloys, and steel; and ceramics such as glasses, potteries, tiles, etc.

For the primary paint of the present invention, solid or liquid state paints can be used. The solid state paint largely consists of thermosetting resin and curing agents, while the liquid state paint includes a curing type containing solvents within solid state paint; a drying type forming film by evaporating solvents; a photocurable type including monomer and photo initiator. These resins are one of the components for at least one kind of primary paints. Some other components such as leveling agents, wetting agents, adhesion promoters, ultraviolet stabilizers, and colorants can be included for the present invention, if needed.

The resins above are not necessarily restricted. That is, if they are suited for the purpose of the present invention, anything among them can be used and selected depending on materials. For instance, those that can be used as curable resins are melamine, polyester, epoxy, acryl, acryl melamine, hybrid of polyester and epoxy, silicone typed thermosetting resin, photocurable resin, etc. As curing agents, in case of polyester, 1,3,5-triglycidyl isocyanurate and block isocyanate can be used. In case of epoxy, ammonia, amine types such as diethylenetriamine, hexamethylenetriamine, methandiamine, xylenediamine, isophoronediamine, and dicyandiamide can be used. In case of acryl, carboxylic acid of polyester type can be used. Those as solvent drying resins are polyurethane, acrylic polymer, polyvinyl chloride, nitrocellulose, polyvinyl alcohol, or poly butyral. For photocurable resins, there are acrylic oligomer such as urethane acrylate, epoxy acrylate, polyester acrylate, and silicone acrylate, and mono-functional or multi-functional acrylic monomer such as hydroxyethyl acrylate, hydroxyethyl methacrylate, 1,6-hexanediol acrylate, and vinyl ether monomer such as butandiol monovinylether and triethyleneglycol divinylether. For photo initiators, 1-hydroxycyclohexylphenylketone, 2-hydroxy-2-methyl-1-phenylpropane-1-on, 2,2-dimethoxy-1,2-diphenylethanone, etc can be used.

Also, leveling agents and wetting agents are used to prevent pinholes and craters, which affect high-reflecting specular surfaces, and to form smooth primary coating. The examples are Surfynol series by Air Product, TEGOwet series by Deguessa, BYK series by BYK, Glide series by Deguessa, EFKA 3000 series by EFKA, DSX series by Cognis, Powdermate series by TROY, acryl oligomer by KSCNT, etc. For adhesion promoters, there are wax emulsion, amide wax, carnauba wax, PE wax, and silane coupling agents such as trimethoxy propyl silane, vinyl trimethoxy silane, mercapto propyl trimethoxy silane. Titania, zirconic, and aluminium type coupling agents can be used, too. For ultraviolet stabilizers, there are derivatives of benzophenone type, benzotriazole type, nickel chelater, salicylic acid type, benzoate type, and hals type. Ciba Specialty's TINUVIN series and Chimassorb series are the representative examples.

The primary painting composition through such process now forms a coating layer with high illuminance by spray, dip, and roll coating.

Step (ii):

This step is where silver specular surface reflecting layer (2) is formed after the composition for reflecting layers is coated and heated on the primary layer (1), which was prepared in Step (i).

The composition for reflecting layers is the same as what was describe before.

As for the coating methods, any methods can be used including brushing, spray coating, dip coating, roll coating, spin coating, or printing such as inkjet printing, offset printing, screen printing, pad printing, Gravure printing, Flexo printing, Riso printing, etc. Any coating methods can be used and selected depending on the material's form and quality.

The silver specular surface can be now obtained from the material coated by such methods through the process including oxidation or reduction, annealing, infrared ray, ultraviolet, electronic layer, laser treatment, etc.

The after-treatment process can be done through heat treatment at the usual inert atmosphere, but it can be also done in air, nitrogen, and carbon monoxide, or in mixed gases containing hydrogen, air and other inert gases, if necessary. Heat treatment is usually done at between 80° C. and 400° C., desirably at between 90° C. and 300° C., or more desirably at between 100° C. and 250° C. In addition, heating twice at each low and high temperature within the above temperature range helps the uniformity of film. For instance, it is good that they are treated at 80~150° C. for 1~30 minutes and then again at 150~300° C. for 1~30 minutes.

Step (iii):

This step is where transparent coating is applied to protect the reflecting layer (2) that was prepared above. The fluid for transparent coating used to form the transparent finish layer (3) is not necessarily restricted. That is, anything among them can be used once they are suited for the purpose of the present invention, and the transparency of film after coating should be more than 90%, with great resistance against heat, weather, corrosion, and salt water. The fluid for transparent coating here may include a separate reductant and the examples are hydrazine, acetichydrazide, sodium or potassium borohydride, trisodium citrate; amine compounds such as methyl diethanolamine and dimethylamine borane; metal salts such as ferric chloride monobasic and iron sulfate; hydrogen, hydrogen iodide, carbon monoxide; aldehyde compounds such as formaldehyde and acetealdehyde; organic compounds such as glucose, ascorbic acid, salicylic acid, tannic acid, pyrogallol, and hydroquinone. For ultraviolet stabilizers, like in primary paints, there are derivatives of benzophenone type, benzotriazole type, nickel chelater, salicylic acid type, benzoate type, and hals type. Ciba Specialty's TINUVIN series and Chimassorb series are the representative examples.

Figure 2:
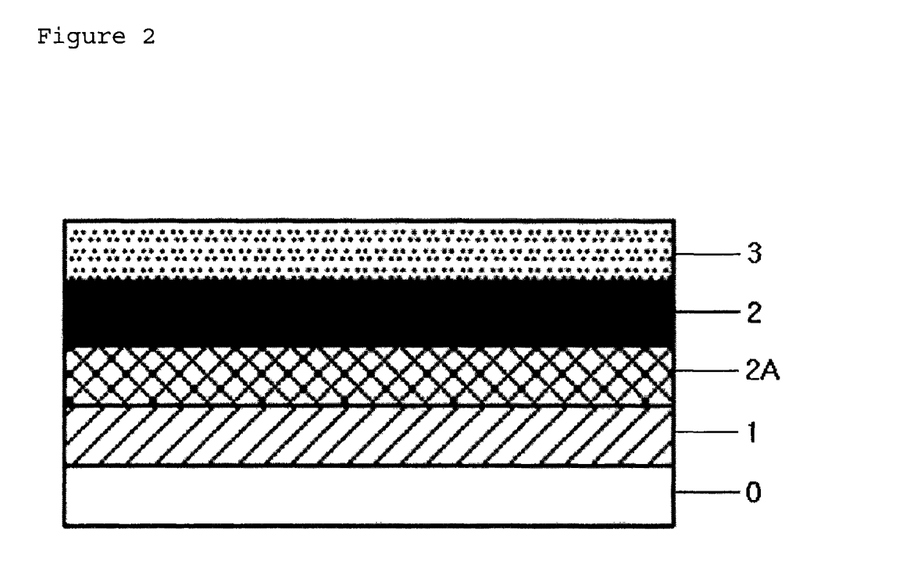
FIG. 2 is a cross section of the reflecting layer that is composed of a primary coating layer (1), a pre-coat layer (2A), a reflecting layer (2), and a transparent finish coating layer (3).

FIG. 2 is a cross section of the reflecting layer that is composed of a primary coating layer (1), a pre-coat layer (2A), a reflecting layer (2), and a transparent finish coating layer (3).

For the present invention, in case there is no adhesion force between the primary coating layer (1) and the reflecting layer (2), or in case silver specular reflecting layers with high gloss and reflectance are not well formed, a pre-coat layer (2A) can be made, after coating and drying a separate primer between them, to improve the adhesion force and gloss. The primer is liquid paint and can be used without specific restrictions. That is, anything can be used if they are suited for the purpose of the present invention. For instance, those that are used as primers are alkyd resins, polyester resins, silicone resins, polyurethane resins, epoxy resins, phenol resins, polyamide resins, melamine resins, acryl resins, unsaturated polyester resins, and polyvinyl butyral resins. For colorants, the white pigment of metal oxide is used such as silane oxide, titanium dioxide, zirconium oxide, and magnesium oxide.

Figure 3:
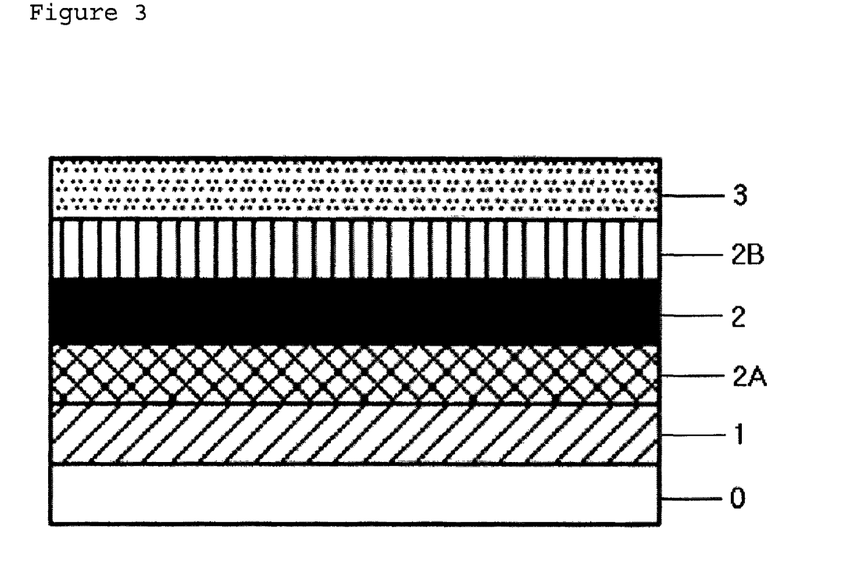
FIG. 3 is a cross section of the reflecting layer that is composed of primary coating layer (1), a pre-coat layer (2A), a reflecting layer (2), a post-coat layer (2B) and a transparent finish coating layer (3).
Figure 4:
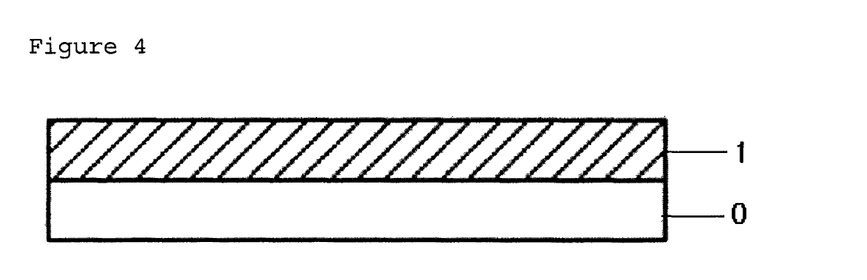
FIG. 4 is a cross section of lamp reflector forming process by laminating of a supporter (10) and the reflecting layer, according to Example 9 of the present invention.
Figure 5:
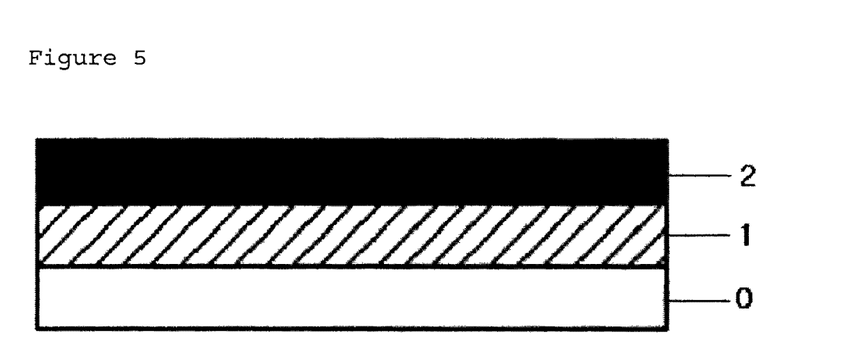
FIG. 5 is a cross section of lamp reflector forming process by laminating of a supporter (10) and the reflecting layer, according to Example 9 of the present invention.
Figure 6:
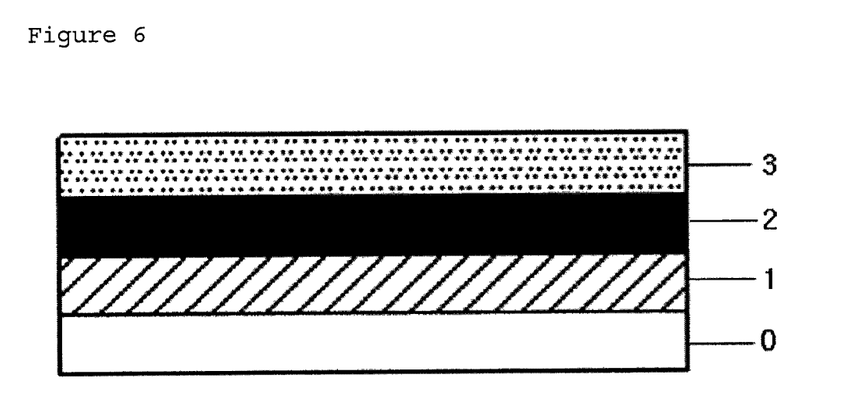
FIG. 6 is a cross section of lamp reflector forming process by laminating of a supporter (10) and the reflecting layer, according to Example 9 of the present invention.
Figure 7:
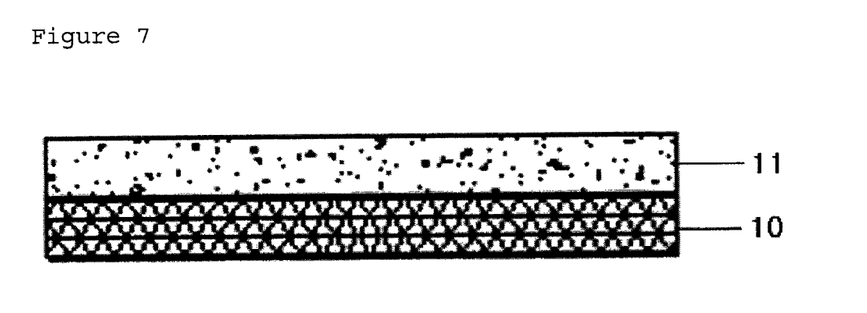
FIG. 7 is a cross section of lamp reflector forming process by laminating of a supporter (10) and the reflecting layer, according to Example 9 of the present invention.
Figure 8:
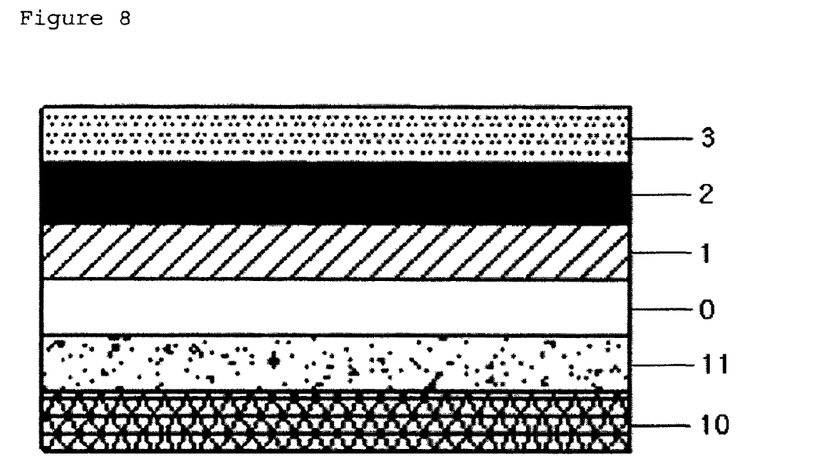
FIG. 8 is a cross section of lamp reflector forming process by laminating of a supporter (10) and the reflecting layer, according to Example 9 of the present invention.
Figure 9:
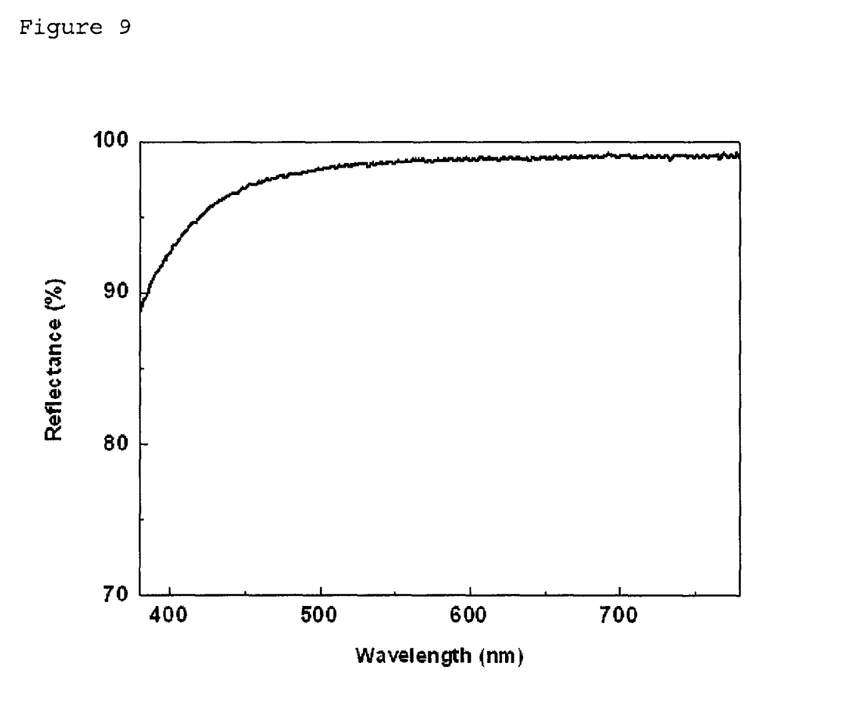
FIG. 9 is a reflectance graph of Example 9 in the range of visible ray.
Figure 10:
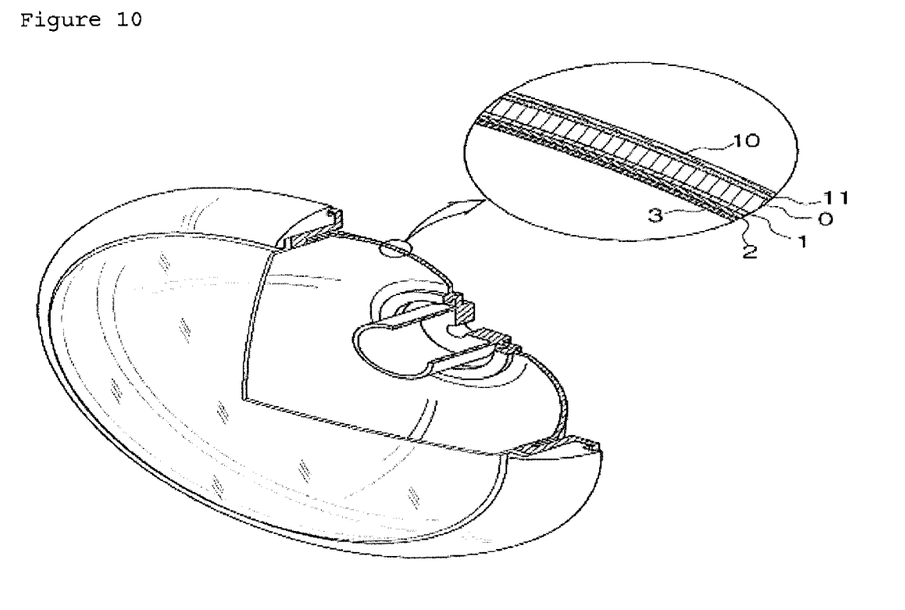
FIG. 10 is a perspective view and partial cross section of a headlight where the reflecting layer according to the present invention is formed.

FIG. 3 is a cross section of the reflecting layer that is composed of primary coating layer (1), a pre-coat layer (2A), a reflecting layer (2), a post-coat layer (2B) and a transparent finish coating layer (3).

In the present invention, a reflecting layer can be made by forming transparent finish coating, after a post-coat layer (2B) is prepared by doing another transparent coating on the reflecting layer (2), in order to improve the adhesion force between the high-gloss reflecting layer (2) and the transparent finish coating layer (3) and control transparency and color change. Those used to form the post-coat layer (2B) are polymer resins such as water dispersed polyurethane resins, silicone resins and acryl resins and metal compounds including silane coupling agents, zirconium coupling agents, titanium coupling agents, and metal precursors. There is no restriction of use, once they have high transparency and the ability to form thin film. Meanwhile, when there are silver complexes, which have not been completely heated on the reflecting layer (2), they can be treated by reductants. The examples of reductants are hydrazine, acetichydrazide, sodium or potassium borohydride, trisodium citrate; amine compounds such as methyl diethanolamine and dimethylamine borane; metal salts such as ferric chloride monobasic and iron sulfate; hydrogen, hydrogen iodide, carbon monoxide; aldehyde compounds such as formaldehyde and aceteal-dehyde; organic compounds such as glucose, ascorbic acid, salicylic acid, tannic acid, pyrogallol, and hydroquinone.

FIG. 4 through FIG. 8 are the cross sections of lamp reflector forming process by laminating of a supporter (10) and the reflecting layer, according to Example 9 of the present invention.

The present invention may include another step where the reflecting layer is laminated and adhered to the supporter (10), which is selected among metal or ceramic layers, if necessary. Since adhesion among layers is poor, an adhesive (11) is usually used without specific restrictions. That is, anything can be used, once they are suited for the purpose of the present invention and if they have no heat deflection in the reflecting layer after laminating and keep the excellent adhesive force. The examples of adhesives are polyester type, epoxy type, acryl type, and cyanoacryl type adhesives.

EXPLANATION OF SYMBOLS FOR MAIN PART OF THE FIGURES

0: material, 1: primary coating layer, 2 reflecting layer, 3: transparent finish coating layer, 2A: pre-coat layer, 2B: post-coat layer, 10: supporter, 11: adhesive

BEST MODE

Hereinafter, the present invention is described in more detail based on the following examples. But, these examples are not intended to limit the scope of the present invention.

EXAMPLE

Example 1

The following materials were all put into Henschel mixer and uniformly mixed: 350.0 g of solid state polyester having an acid value of 30~70 mg (KOH/g) as curable resin; 350.0 g of solid state epoxy of EEW 600~1500 as bisphenol A type; 10.0 g of Powdermate (amide modified polyether, by Troy) as a leveling agent; 8.0 g of Amidewax (by Lubrizol) as an adhesion promoter; 10.0 g of TUVIN405 (by Ciba Specialty) as a ultraviolet stabilizer; 200.0 g of titanium dioxide as a (white) colorant. After extrusion, they were powdered into suitable particle size. Then the powder was coated onto the aluminum plate using the Corona electrostatic spray gun and treated in the 150° C. oven for 30 minutes and cured. Thus, a primary layer with great smoothness was obtained.

Example 2

The following materials were all put into Henschel mixer and uniformly mixed: 350.0 g of solid state polyester having an acid value of 30~70 mg (KOH/g) as curable resin; 350.0 g of solid state epoxy of EEW 600~1500 as bisphenol A type; 10.0 g of acryl oligomer (made by KS CNT) as a leveling agent; 10.0 g of TUVIN405 (made by Ciba Specialty) as a ultraviolet stabilizer; 200.0 g of titanium dioxide as a (white) colorant. After extrusion, they were powdered into suitable particle size. Then the powder was coated onto the aluminum plate using the Corona electrostatic spray gun and treated at 150° C. for 30 minutes and cured. Thus, a primary layer with great smoothness was obtained.

Example 3

On the primary layer prepared in Example 2, KR255 (silicone curable resin, made by Shin-Etsu Chemical Co., Ltd.)

was coated using the spray gun and treated at 150° C. for 3 hours. Thus, a pre-coat layer (2A) was obtained.

Example 4

65.0 g (215 mmol) of 2-ethylhexyl ammonium 2-ethyl carbamate was dissolved in 150.0 g of isopropanol within a 500 ml Schlenk flask equipped with an agitator. Then, 20.0 g (86.2 mmol) of silver oxide was added to react at room temperature. It was observed that the color of the reacted solution was gradually changing from black slurry to transparent while the reaction was progressing as a complex was being obtained. Two hours later, it was changed to the completely colorless and transparent solution. In this solution, 2.5 g of 2-hydroxy-2-methylenepropylamine was added with 85.0 g of n-butanol and 50.0 g of amyl alcohol as solvents and agitated. Then it was filtered through the 0.45 μm membrane filter. Then, a composition for silver coating fluid was obtained, which contains 4.87 weight percent of silver according to the result of thermogravimetric analysis. The composition for silver coating fluid was coated on the aluminum plate obtained in Example 1 using the spray gun. After heat treatment in the infrared ray oven for 10 minutes, a reflecting layer with high reflectance was obtained. Table 1 shows properties on the adhesive force between this reflecting layer and the primary layer and their reflectance.

Example 5

The composition for silver coating fluid prepared in Example 4 was coated on the aluminum plate obtained in Example 2 using the spray gun. After heat treatment in the infrared ray oven for 10 minutes, a reflecting layer with high reflectance was obtained. Table 1 shows properties on the adhesive force between this reflecting layer and the primary layer and their reflectance.

Example 6

The composition for silver coating fluid prepared in Example 4 was coated on the aluminum plate obtained in Example 3 using the spray gun. After heat treatment in the infrared ray oven for 10 minutes, a reflecting layer with high reflectance was obtained. Table 1 shows properties on the adhesive force between this reflecting layer and the primary layer and their reflectance.

TABLE 1

Properties of silver specular layer prepared in Examples

| Example | Adhesive force among layers | reflectance (R %) |
| --- | --- | --- |
| Example 4 | ○ | 97.3 |
| Example 5 | Δ | 96.8 |
| Example 6 | ○ | 96.7 |

(1) Adhesive force test among layers: using a cutter knife, the reflecting layer is graduated vertically and horizontally in 11 points respectively at 2 mm intervals to leave 100 marks on. A cellophane tape (brand name: 3M, product name: Scotch) is adhered to the silver specular reflecting layer and peeled. Then, the transcription state of silver film onto adhesive layer is tested.
○: no silver film is transcribed onto the adhesive layer of the tape
Δ: some part of silver film is transcribed onto the adhesive layer of the tape and separated from mechanism
x: most part of silver film is transcribed onto the adhesive layer of the tape and separated from mechanism (2) Reflectance: the reflecting layer is cut into squares 5 cm in width and length respectively to make three samples. Luminous reflectance is measured using standard illuminant to get the average. (After measuring the chromaticity coordinate of X, Y, and Z, it is defined as Y among them; ASTM E 1651-94)

Example 7

On the aluminum plate where high reflecting silver specular layer is formed in Example 4, Spitight500 Plus (made by Samhwa Paint), finish coating fluid containing acryl silicone type resin is coated using the spray gun. After heat treatment in the oven at 150° C. for 1 hour, it formed a transparent finish coating layer and then a reflecting layer was obtained. Table 2 shows the properties of the reflecting layer prepared by such method.

Example 8

On the aluminum plate where high reflecting silver specular layer is formed in Example 4, SR 2410 (made by Toray Dow Corning Silicone Co., Ltd.), finish coating fluid containing silicone type resin is coated using the spray gun. After heat treatment in the oven at 150° C. for 1 hour, it formed a transparent finish coating layer and then a reflecting layer was obtained. Table 2 shows the properties of the reflecting layer prepared by such way.

Example 9

33.8 g (111.7 mmol) of 2-ethylhexyl ammonium 2-ethyl carbamate and 30.4 g (146 mmol) of isobutylammonium isobutylcarbonate were dissolved in 16.0 g of isopropanol within a 500 ml Schlenk flask equipped with an agitator. Then, 20.0 g (86.2 mmol) of silver oxide was added to react at room temperature. It was observed that the color of the reacted solution was gradually changing from black slurry to transparent while the reaction was progressing as a complex was being obtained. Two hours later, it was changed to the completely colorless and transparent solution. In this solution, 2.5 g of 2-hydroxy-2-methylenepropylamine was added as a stabilizer and agitated. Then it was filtered through the 0.45 μm membrane filter. Thus, a composition for silver coating fluid was obtained, which contains 20.56 weight percent of silver according to the result of thermogravimetric analysis. The composition for silver coating fluid was coated on PET film, where acryl primary coating is treated, using Gravure printing and baked at 150° C. for 1 minute. Then a reflecting layer with high reflectance was obtained. Transparent finish coating, composed of water dispersed polyurethane resin, was applied to the reflecting layer, which was dried at 60° C. for 2 minutes. On the other side of coating, TKS-500 (adhesive, made by Vixxol A&C) was coated. After laminating on the aluminum plate, a lamp reflector was obtained.

TABLE 2

Properties of the reflecting layer prepared in Examples

| Example | salt spray test | weather resistance | durability | reflectance (%) |
|---|---|---|---|---|
| Example 7 | ○ | ○ | ○ | 97.1 |
| Example 8 | Δ | ○ | ○ | 96.8 |
| Example 9 | ○ | ○ | ○ | 97.3 |

(1) salt spray test: salt water (pH: 6.5~7.2) is sprayed onto the reflecting layer at 15~35° C. for two hours and left for 20~22 hours. The same cycle is repeated three times for testing.
○: no change in the reflecting layer
Δ: some change in the reflecting layer
x: big change in the reflecting layer
(2) weather resistance test: UV of 300 W at 80° C. is observed for 50 hours to determine any change in the reflecting layer
○: no change in the reflecting layer
Δ: some change in the reflecting layer
x: big change in the reflecting layer
(3) durability test: the reflecting layer is kept in the temperature and humidity chamber at 60° C. and 90% humidity for 500 hours to determine any change.
○: no change in the reflecting layer
Δ: some change in the reflecting layer
x: big change in the reflecting layer
(4) reflectance: the reflecting layer is cut into squares 5 cm in width and length respectively to make three samples. Luminous reflectance is measured using standard illuminant to get the average. (After measuring the chromaticity coordinate of X, Y, and Z, it is defined as Y among them; ASTM E 1651-94)

INDUSTRIAL APPLICABILITY

As described above, the present invention can provide silver coating compositions and its preparation method of reflecting layers using the same, which can produce high-reflecting layers after forming primary coating layers that promote illuminance and adhesive force of reflecting materials such as plastic, ceramic, metal, etc., and then forming high-reflecting layers by coating silver coating fluid including silver complexes with distinct structures, followed by transparent-coating to protect the silver specular surface.

Also, the present invention can provide silver coating compositions and preparation methods of reflecting layers using them, which can be mass manufactured with no risk of air pollution or water contamination and have low defective proportions and inexpensive production costs due to simple manufacturing process.

The invention claimed is:

1. Compositions for forming reflecting layer containing silver complexes that are obtained by the reaction between at least one silver compound of Formula 1 and one or more than two ammonium carbamate or ammonium carbonate based compounds selected from Formula 2 to 4:

[Formula 1]

[Formula 2]

[Formula 3]

[Formula 4]

[In the formula above,
X is a substituted group selected from the group consisting of oxygen, sulfur, halogen, cyano, cyanate, carbonate, nitrate, nitrite, sulfate, phosphate, thiocyanate, chlorate, perchlorate, tetrafluoro borate, acetylacetonate, carboxylate and their derivatives, n is an integer of 1~4, $R_1$ to $R_6$ are substituted groups independently selected from the group consisting of hydrogen, C1-C30 of aliphatic or cycloaliphatic alkyl group or aryl or aralkyl group, alkyl and aryl group substituted with functional group, heterocyclic compound, polymer compound and their derivatives, and $R_1$ to $R_6$ are not all hydrogen.]

2. The compositions for forming reflecting layer of claim 1, wherein said silver complexes have the structure of Formula 5:

[Formula 5]

[A is the compound of Formula 2 to 4, and m ranges in 0.5~1.5.]

3. The compositions for forming reflecting layer of claim 1, wherein said silver compound is one or more than two mixture selected from the group consisting of silver oxide, silver thiocyanate, silver cyanide, silver cyanate, silver carbonate, silver nitrate, silver nitrite, silver sulfate, silver phosphate, silver perchlorate, silver tetrafluoro borate, silver acetylacetonate, silver acetate, silver lactate, silver oxalate and their derivatives.

4. The compositions for forming reflecting layer of claim 1, wherein $R_1$ to $R_6$ are independently selected from the group consisting of hydrogen, methyl, ethyl, propyl, isopropyl, butyl, isobutyl, amyl, hexyl, ethylhexyl, heptyl, octyl, isooctyl, nonyl, decyl, dodecyl, hexadecyl, octadecyl, docodecyl, cyclopropyl, cyclopentyl, cyclohexyl, allyl, hydroxy, methoxy, hydroxyethyl, methoxyethyl, methoxypropyl, cyanoethyl, ethoxy, buthoxy, hexyloxy, methoxyethoxyethyl, methoxyethoxyethoxyethyl, hexamethyleneimine, morpholine, piperidine, piperazine, ethylenediamine, propylenediamine, hexamethylenediamine, triethylenediamine, pyrrol, imidazol, pyridine, carboxymethyl, trimethoxysilylpropyl, triethoxysilylpropyl, phenyl, methoxyphenyl, cyanophenyl, phenoxy, tolyl, benzyl, polyallylamine, polyethyleneimine and their derivatives, and $R_1$ to $R_6$ are not all hydrogen.

5. The compositions for forming reflecting layer of claim 1, wherein said ammonium carbamate or ammonium carbonate based compounds are one or more than two mixture selected from the group consisting of ethylammonium ethylcarbamate, isopropylammonium isopropylcarbamate, n-butylammonium n-butylcarbamate, isobutylammonium isobutylcarbamate, t-butylammonium t-butylcarbamate, 2-ethylhexylammonium 2-ethylhexylcarbamate, octadecylammonium octadecylcarbamate, 2-methoxyethylammonium 2-methoxyethylcarbamate, 2-cyanoethylammonium 2-cyanoethylcarbamate, dibutylammonium dibutylcarbamate, dioctadecylammonium dioctadecylcarbamate, methyldecylammonium methyldecylcarbamate, hexamethyleneimineammonium hexamethyleneiminecarbamate, morpholinium morpholinecarbamate, pyridinium ethylhexylcarbamate, triethylenediaminium isopropylbicarbamate, benzylammonium benzylcarbamate, triethoxysilyipropylammonium triethoxysilylpropylcarbamate, ethylammonium ethylcarbonate, isopropylammonium isopropylcarbonate, isopropylammonium bicarbonate, n-butylammonium n-butylcarbonate, isobutylammonium isobutylcarbonate, t-butylammonium t-butylcarbonate, t-butylammonium bicarbonate, 2-ethylhexylammonium 2-ethylhexylcarbonate, 2-ethylhexylammonium bicarbonate, 2-methoxyethylammonium 2, methoxyethylcarbonate, 2-methoxyethylammonium bicarbonate, 2-cyanoethylammonium 2-cyanoethylcarbonate, 2-cyanoethylammonium bicarbonate, octadecylammonium octadecylcarbonate, dibutylammonium dibutylcarbonate, dioctadecylammonium dioctadecylcarbonate, dioctadecylammonium bicarbonate, methyldecylammonium methyldecylcarbonate, hexamethyleneimineammonium hexamethyleneiminecarbonate, morpholineammonium morpholinecarbonate, benzylammonium benzylcarbonate, triethoxysilylpropylammonium triethoxysilylpropylcarbonate, pyridinium bicarbonate, triethylenediaminium isopropylcarbonate, triethylenediaminium bicarbonate and their derivatives.

6. The compositions for forming reflecting layer of claim 1, wherein said compositions more comprise a single or mixed material of solvents, stabilizers, leveling agents and film assistants.

7. The compositions for forming reflecting layer of claim 6, wherein said solvents are one or more than two mixture selected from the group consisting of water, alcohol, glycol, acetate, ether, ketone, aliphatic hydrocarbon, aromatic hydrocarbon and halogen substituted hydrocarbon solvent.

8. The compositions for forming reflecting layer of claim 6, wherein said solvents are one or more than two mixture selected from the group consisting of water, methanol, ethanol, isopropanol, butanol, ethyleneglycol, glycerine, ethyl acetate, butyl acetate, carbitol acetate, diethyl ether, tetrahydrofuran, dioxane, methyl ethyl ketone, acetone, hexane, heptane, benzene, toluene, chloroform, methylene chloride, carbontetrachloride or mixed solvents of the above.

9. The compositions for forming reflecting layer of claim 6, wherein said stabilizers are at least one selected from the group consisting of amine compounds, Formula 2, Formula 3, Formula 4 or mixture of at least one of them, phosphorus compounds and sulfur compounds.

10. The compositions for forming reflecting layer of claim 9, wherein said phosphorus compounds are selected from the compounds represented as Formula 6 or Formula 7:

[Formula 6]

[Formula 7]

[In the formula above, R indicates alkyl or aryl group of carbon number 1~20.]

11. The compositions for forming reflecting layer of claim 9, wherein said sulfur compounds are selected from the group consisting of butan thiol, n-hexanethiol, diethyl sulfide or tetrahydrothiophene.

12. The compositions for forming reflecting layer of claim 6, wherein said film assistants are at least one selected from the group consisting of organic acid, organic acid ammonium salt or organic acid metal salt.

13. Preparation method of reflecting layers comprising the steps of: (i) forming a primary coating layer, which improves the adhesion force of silver specular coating layers, by coating a primary paint on the surface of reflecting materials, and (ii) forming a reflecting layer coating a high-reflecting specular surface on the primary coating layer using the compositions for forming reflecting layer of claim 1.

14. The preparation method of reflecting layers of claim 13, wherein said method more comprises the step of: (iii) forming a transparent finish coating after said step (ii) forming the reflecting layer.

15. The preparation method of reflecting layers of claim 13, wherein said primary paint comprises a thermosetting resin or a photocurable resin.

16. The preparation method of reflecting layers of claim 15, wherein said thermosetting resin is melamine, polyester, epoxy, acryl, acryl melamine, hybrid of polyester and epoxy or silicone typed resin.

17. The preparation method of reflecting layers of claim 15, wherein said photocurable resin is acrylic oligomer, monofunctional or multi-functional acrylic monomer and vinyl ether monomer.

18. The preparation method of reflecting layers of claim 13, wherein said primary paint comprises polyurethane, acrylic polymer, polyvinyl chloride, nitrocellulose, polyvinyl alcohol or poly butyral.

19. The preparation method of reflecting layers of claim 13, wherein said coating method is brushing, spray coating, dip coating, roll coating, spin coating, inkjet printing, offset printing, screen printing, pad printing, Gravure printing, Flexo printing or Riso printing.

20. The preparation method of reflecting layers of claim 14, wherein the transparent coating solution for forming said transparent finish coating comprises a reductant.

21. The preparation method of reflecting layers of claim 20, wherein said reductant is selected from the group consisting of hydrazine, acetichydrazide, sodium, potassium borohydride, trisodium citrate, amine compound selected from methyl diethanolamine and dimethylamine borane, metal salt selected from ferric chloride monobasic and iron sulfate, hydrogen, hydrogen iodide, carbon monoxide, aldehyde compound selected from formaldehyde and acetealdehyde, glucose, ascorbic acid, salicylic acid, tannic acid, pyrogallol and hydroquinone.

22. The preparation method of reflecting layers of claim 13, wherein said method more comprises the step of: forming a pre-coat layer by coating and drying a primer between step (i) and step (ii).

23. The preparation method of reflecting layers of claim 22, wherein said primer is selected from the group consisting of alkyd resin, polyester resin, silicone resin, polyurethane resin, epoxy resin, phenol resin, polyamide resin, melamine resin, acryl resin, unsaturated polyester resin and polyvinyl butyral resin.

24. The preparation method of reflecting layers of claim 14, wherein said method more comprises the step of: forming a post-coat layer by doing said transparent coating between step (ii) and step (iii).

25. The preparation method of reflecting layers of claim 24, wherein said transparent coating solution is polymer resin selected from water dispersed polyurethane resin, silicone resin and acryl resin, or metal compound selected from silane coupling agent, zirconium coupling agent, titanium coupling agent and metal precursor.

* * * * *